(12) United States Patent
Lebet

(10) Patent No.: US 8,926,625 B2
(45) Date of Patent: Jan. 6, 2015

(54) SURGICAL DEVICE

(76) Inventor: Alain Lebet, Lausanne (CH)

(*) Notice: Subject to any disclaimer, the term of this patent is extended or adjusted under 35 U.S.C. 154(b) by 203 days.

(21) Appl. No.: 13/259,496

(22) PCT Filed: Mar. 29, 2010

(86) PCT No.: PCT/IB2010/000830
§ 371 (c)(1),
(2), (4) Date: Sep. 23, 2011

(87) PCT Pub. No.: WO2010/109327
PCT Pub. Date: Sep. 30, 2010

(65) Prior Publication Data
US 2012/0022545 A1    Jan. 26, 2012

(30) Foreign Application Priority Data

Mar. 27, 2009 (GB) .................................. 0905337.2
Jul. 31, 2009 (GB) .................................. 0913434.7
Nov. 27, 2009 (GB) .................................. 0920882.8

(51) Int. Cl.
| | | |
|---|---|---|
| A61B 17/56 | (2006.01) | |
| A61B 17/88 | (2006.01) | |
| A61B 17/92 | (2006.01) | |
| B01D 46/00 | (2006.01) | |
| B01D 46/42 | (2006.01) | |
| A61B 17/00 | (2006.01) | |
| A61F 2/34 | (2006.01) | |

(52) U.S. Cl.
CPC .............. *A61B 17/92* (2013.01); *B01D 46/008* (2013.01); *B01D 46/4272* (2013.01); *A61B 2017/00544* (2013.01); *A61B 2017/924* (2013.01); *A61B 2017/925* (2013.01); *A61F 2/34* (2013.01); *B01D 2279/65* (2013.01)
USPC ........................................... 606/99; 606/100

(58) Field of Classification Search
USPC ............... 606/79, 86 R, 90, 91, 99, 100, 128; 623/22.12
See application file for complete search history.

(56) References Cited

U.S. PATENT DOCUMENTS

| | | | | |
|---|---|---|---|---|
| 4,810,272 A | * | 3/1989 | Overby ........................... 55/420 |
| 5,201,750 A | * | 4/1993 | Hocherl et al. ............... 606/180 |
| 5,474,559 A | * | 12/1995 | Bertin et al. .................... 606/89 |
| 5,722,962 A | * | 3/1998 | Garcia .......................... 604/264 |
| 5,728,102 A | * | 3/1998 | Feingold et al. .............. 606/107 |
| 5,906,623 A | | 5/1999 | Peterson |
| 5,980,528 A | | 11/1999 | Salys |
| 7,470,274 B2 | | 12/2008 | Lebet |
| 2003/0000774 A1 | | 1/2003 | Highley |
| 2005/0010189 A1 | * | 1/2005 | Toomey et al. ............... 604/403 |
| 2006/0069395 A1 | | 3/2006 | Lebet |
| 2006/0100553 A1 | | 5/2006 | Lodin |
| 2008/0195103 A1 | * | 8/2008 | Lawis et al. .................... 606/80 |
| 2009/0118741 A1 | | 5/2009 | Lebet |

FOREIGN PATENT DOCUMENTS

FR  2 851 153 A1  8/2004

* cited by examiner

*Primary Examiner* — Michael T Schaper
*Assistant Examiner* — Tracy Kamikawa
(74) *Attorney, Agent, or Firm* — Woods Patent Law

(57) ABSTRACT

The invention relates to a surgical device, the device comprising a probe part and means to generate a Shockwave in the probes sufficient to separate, adjust of attach two or more, parts when the probe is applied to one of the part in vivo, the arrangement being such as to allow the application of a Shockwave that is regulated in amplitude and repeatable.

22 Claims, 4 Drawing Sheets

SURGICAL DEVICE

The present invention relates to a surgical device. In particular the invention relates to a surgical device for use in surgical procedures involving the separation, adjustment and/or attachment in vivo, of parts comprising different materials.

A number of different surgical procedures require the application of force by a surgeon to a structure, for separation adjustment or attachment of parts. Examples of such procedures are Total Hip Arthroplasty (THA), implant revision/adjustment insertion of orthopaedic nails and removal of metallic parts from bone.

Various problems exist with current surgical techniques used in such procedures, most of which stem from the fact that the techniques require the exertion of manual force by the surgeon in a manner that is difficult to control and regulate and difficult to repeat with consistency, requiring considerable manual skill.

As an example, Total Hip Arthroplasty (THA) is a surgical procedure in which the hip joint is replaced by a prosthetic implant. FIGS. 1 and 2 show cut-away and schematic views of a common type of prosthetic implant in place in a joint of a patient. The implant consists of two main parts, a stem A with a ball head (B) that is disposed in the femur and a socket C that is fixed into the pelvis. In one type of implant (FIG. 2) the socket C comprises a metal cup D that has a liner or insert E that can be made from a plastics material or increasingly commonly, a ceramics material. Such surgery is generally conducted to relieve arthritis pain or correct severe physical joint damage for example as part of a hip fracture treatment. Currently, to insert socket C into the pelvis, and also to insert metal cup D and insert E in place the surgeon is required to use a metal stick and hammer. These implements are used to force the parts into their required places, and also to adjust their positions and orientations when in place. The stick is placed upon the parts to be inserted/adjusted and a blow is delivered to its proximal end with the hammer. The magnitude of the shock to be imparted is judged by the surgeon, but the subjective nature of the exercise inevitably means that in many cases the first blow is either too weak or too strong. It is clearly the case that the minimum number of blows possible should be used for the safety and comfort of the patient.

Over time, prosthetic implants can themselves cause problems. In the case of implant loosening, sepsis and implant wear, parts or all of the prosthetic implant must be replaced, known as revision.

When revision of an insert E or a head B is required, the surgical technique currently used involves the application of a shock to the implant by the surgeon, again using a metal stick and a hammer, the idea being to loosen the insert for removal from the cup. Again the magnitude of the shock to be imparted is judged by the surgeon, but the subjective nature of the exercise inevitably means that in many cases the first applied blow is either too weak or too strong. If the blow is too weak, a further blow is required and the natural tendency for the surgeon is to increase the magnitude of the following blow even if such an increase is not indicated by the situation. It is clearly the case that the minimum number of blows possible should be used to avoid the risk of secondary or ancillary damage. If, on the other hand, the initial blow is too strong, in addition to the risk of ancillary or secondary damage there is a real danger that the insert will be broken. Insert breakage is a major problem because if it is broken, it is very difficult and time consuming to remove all of the fragments, but to do so is essential. If even a tiny fragment remains in the joint it will accelerate wear. This is a particular problem in the case of ceramic inserts, which are by nature relatively brittle. However, there are cases in which the insert is so firmly wedged or fixed in position that the surgeon has no option but to break it.

Similar problems also exist in procedures where a surgeon is required to exert a manual force to drive a part into another part, for example, in insertion of orthopaedic nails.

It is an object of the present invention to seek to mitigate problems such as these.

In accordance with a first aspect of the invention there is provided a surgical device, the device comprising a probe, and means to generate a shock wave in the probe sufficient to separate or attach two or more parts when the probe is applied to one of the parts, the arrangement being such as to allow the application of a shock wave that is regulated in amplitude and repeatable It is preferred that the shock wave generation means is adapted to generate a shock wave upon each operation, each said shock wave having an amplitude within a reproducible pre-set range.

The shock wave generation means may comprise a striker, means to cause the striker to strike the probe, and a manually operable actuator to actuate the shock wave generation means on manual actuation of the device. The means to cause the striker to strike the probe may include pneumatic, electronic or spring actuation means.

The device may further include means to collect fragments of a part should it break. It is preferred that the fragment collection means comprises a cover, the cover being adapted to surround the or each part to which the probe is applied. The fragment collection means may comprise a pierceable shroud or veil that is adapted to form a closed volume around the or each part, either on its own or in combination with a part of the patient's anatomy, the arrangement being such that the probe can be passed through the shroud or veil without creating an aperture through which egress of fragments can occur. In the case of a device for use in a hip replacement or revision, the fragment collection device may comprise a pierceable cup adapted to be placed over an insert in a socket so as to enclose, either with the socket or the anatomy, the insert.

In accordance with a particularly preferred embodiment, the device is adapted for use in total hip replacement and hip replacement revision procedures.

In embodiments in which the surgical device is a pneumatic surgical device, the surgical device may comprise an exhaust valve through which expelled gas may pass, wherein the exhaust valve adopts an open position when a detachable exhaust filter assembly is attached to the device and the exhaust valve adopts a closed position when a detachable exhaust filter assembly is not attached to the device. In the context of the present invention, an "open" exhaust valve allows gas to be expelled through the exhaust valve whilst a "closed" exhaust valve does not allow gas to be expelled through the exhaust valve.

The detachable exhaust filter assembly blocks contaminants, such as grease, from passing through into the sterile area. It may be attached to the device by any suitable means. For example, the detachable exhaust filter assembly may comprise a screw thread that mates with a complementary screw thread on the device. Alternatively, the detachable exhaust filter assembly may comprise a resiliently deformable element such that the detachable exhaust filter assembly may be pushed onto the device to attach it and the resiliently deformable element may be squeezed to deform its shape as the detachable exhaust filter assembly is pulled away from the device to detach it.

As described above, the exhaust valve is biased towards a closed position unless a detachable exhaust filter assembly is attached to the device. The bias towards a closed position may be achieved by a spring or other biasing means.

As described above, the exhaust valve is maintained in an open position once a detachable exhaust filter assembly is attached to the device. The attachment of the detachable exhaust filter assembly resulting in the opening of the exhaust valve may be achieved by the detachable exhaust filter assembly compressing a part of the exhaust valve when it is attached to the device. For example, the detachable exhaust filter assembly may comprise an inner ring that, when the detachable exhaust filter assembly is attached to the device, pushes against a part of the exhaust valve to cause it to open.

During the cleaning and sterilisation process, the detachable exhaust filter assembly is detached from the device and the exhaust valve is closed thereby blocking the entry of cleaning and sterilisation fluids. Steam sterilisation commonly uses steam at a temperature of 134° C. and a pressure of 3 bars, therefore, it is desirable for the exhaust valve to be able to withstand such conditions when closed.

In embodiments in which the surgical device is a pneumatic surgical device, the surgical device may comprise an entry orifice through which the admitted gas may pass, wherein the entry orifice is impermeable to liquids.

Preferably, the entry orifice also allows gas to be expelled when the pneumatic medical device is not in use. This ensures that the device will not contain pressurised gas during storage.

The entry orifice may be in the form of an entry valve or entry filter. The entry orifice may comprise a hydrophobic material or may comprise Teflon™.

It is also desirable for the entry orifice to be able to withstand the conditions of steam sterilisation (134° C. and 3 bars).

The present invention also encompasses pneumatic surgical devices comprising the exhaust valve, the detachable exhaust filter assembly and the entry orifice.

A detachable exhaust filter assembly suitable for use with a pneumatic surgical device may comprise reversible attachment means and an exhaust filter.

The filter within the detachable exhaust filter assembly may be a biological filter, i.e. a filter that sterilises any gases that pass through it.

It is desirable for the detachable exhaust filter assembly to be disposable since this ensures that each detachable exhaust filter assembly is used with only one patient thereby preventing contamination between patients. A disposable filter assembly may be designed such that it can only be attached to a pneumatic surgical device once to ensure it is not re-used. For example, a part of a fitment that enables the detachable exhaust filter assembly to attach to the pneumatic surgical device may shear as the detachable exhaust filter assembly is detached from the pneumatic surgical device to produce a fitment that no longer enables the detachable exhaust filter assembly to attach to the pneumatic surgical device.

The present invention also encompasses the use of a pneumatic medical device according to the present invention.

Gas may be supplied to a pneumatic surgical device from a gas cartridge or using a supply line, with a gas cartridge or supply line being fitted to such a device during use and being removed or detached when such a device is not in use. The gas admitted to such a device must be admitted through an orifice in the device itself.

Gas may be removed from a pneumatic surgical device using an exhaust line, with the exhaust line being fitted to such a device during use and being detached when such a device when not in use. The gas expelled from such a device must be expelled through an orifice in the device itself.

As with all re-usable medical devices, a pneumatic surgical device must be cleaned and sterilised between uses to prevent infection, however, the cleaning or sterilising fluids should not be allowed to pass through the orifices and enter the device since that may damage the device and impair its function. Commonly, sterilisation caps are used to block the orifices of such devices and prevent the cleaning or sterilising fluids from entering the devices. However, reliance on sterilisation caps is clearly undesirable since the caps may not be correctly positioned or may work loose during the cleaning and sterilising process.

In addition to complications caused during the cleaning and sterilising of pneumatic devices, there is also the matter of the processing of non-sterile gas expelled from such devices. Gases expelled from a pneumatic device may include grease and/or other contaminants, therefore, if such gases were expelled into a sterile area (such as an operating theatre) the gases could contaminate the area. Commonly, the gases expelled from such devices are passed through an exhaust line so that they are removed from the sterile area. However, reliance on an exhaust line is clearly undesirable since the exhaust line may not be correctly positioned or may work loose during the use of the pneumatic medical device.

According to a second aspect of the invention there is provided a method for separating or attaching two or more materials in a surgical procedure, the method comprising applying a shock wave to one said material using a device as described hereinabove.

The method may comprise a total hip replacement or hip replacement revision procedure, and may further comprise the use of fragment collection means In particular, the method may comprise the use of a device as described herein above for the insertion and positioning of implant parts, in particular, an implant metal cup in a pelvis of a patient.

The invention will further be described by reference to the following example and figures, in which.

Figure 1:
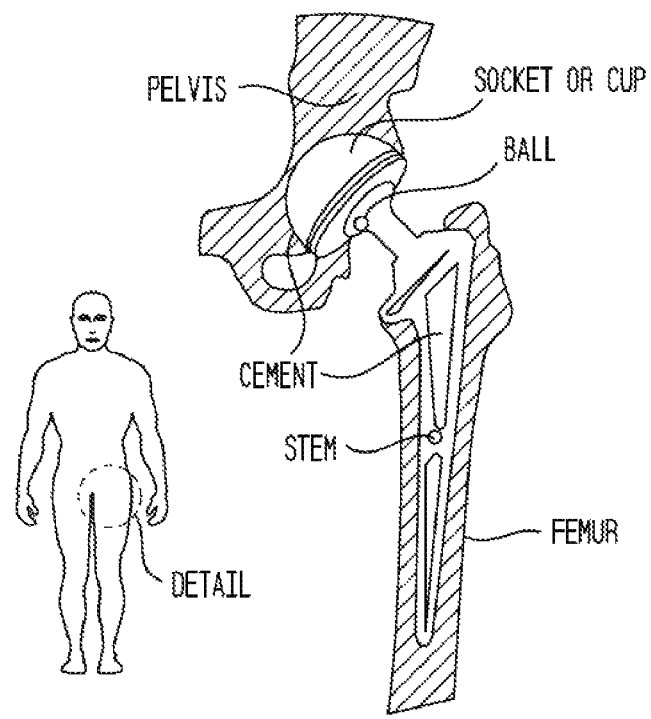
FIG. 1 is a cut-away schematic view of a common type of prosthetic implant upon which the invention can be practised.
Figure 2:
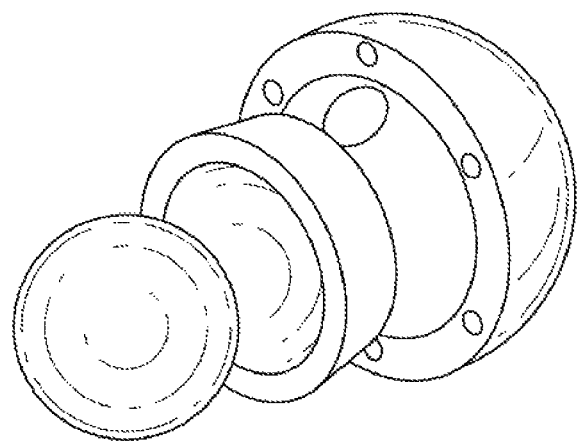
FIG. 2 is an exploded view of a socket assembly.
Figure 3:
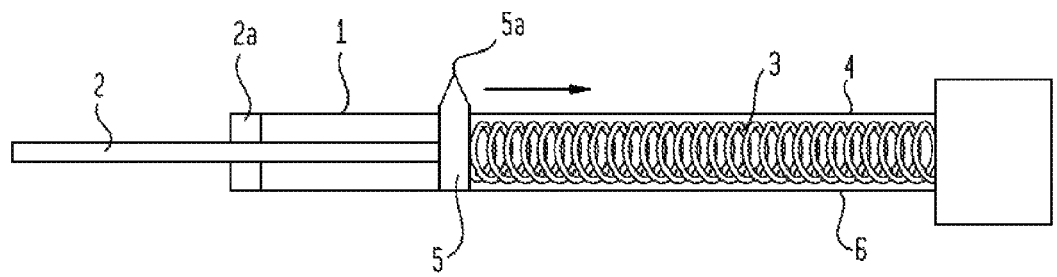
FIG. 3 is a schematic illustration of a device in accordance with one aspect of the invention.

Referring to FIG. 3, there is illustrated a surgical device 1, the device comprising a probe 2, and means 3 to generate a shock wave in the probe sufficient to separate or attach two materials when the probe is applied to one of the materials, the arrangement being such as to allow the application of one or more shock wave that is regulated in amplitude within a set range.

In the present example the device 1 and method according to the invention are illustrated in connection with total hip replacement and hip replacement revision procedures, however it will be appreciated that they have a wider application in any surgical procedure that requires the separation or attachment of two or more components or structures using manual force, in particular for example two or more components or structures having differing Young's moduli.

The device 1 includes shock wave generation means that consists of a simple compressible spring 4, the spring including a striker element 5 mounted at its distal end. The spring 4 is contained within a closed cylindrical body 6 that acts as a guide tube for the striker element 5 upon actuation of the device. The striker element 5 can be for example a disk having a lug extending from the circumference in the plane of the disk and positioned to protrude through a longitudinal cut in the wall of the tube. The spring can be manually compressed in the tube using the lug 5a and at the point of maximum compression the cut can be provided with a notch, the lug seating in the notch at the proximal end of the cut thus maintaining the spring in the compressed condition. As an alternative (not shown), a number of notches can be provided along the cut thereby enabling different degrees of spring compression to be selected.

The probe 2 is set into the distal end of the body 6 such that the striker element 5 can impact directly upon it on release of the spring 4. Alternatively, an intermediate shock transmission member can be provided through which the striker element 5 will act.

The probe 2 may comprise a relatively flexible or rigid metallic rod. The probe 2 can be mounted by means of a removable probe cap 2a so that it can easily be replaced. The probe can be provided with a hardened tip, such as a diamond tip.

Although such an arrangement is mechanically simple, provided that a spring of a sufficient resistance is used such an arrangement will consistently produce a force of set magnitude each time the device 1 is operated, thereby ensuring that neither too little nor too large a force is applied.

Figure 5:
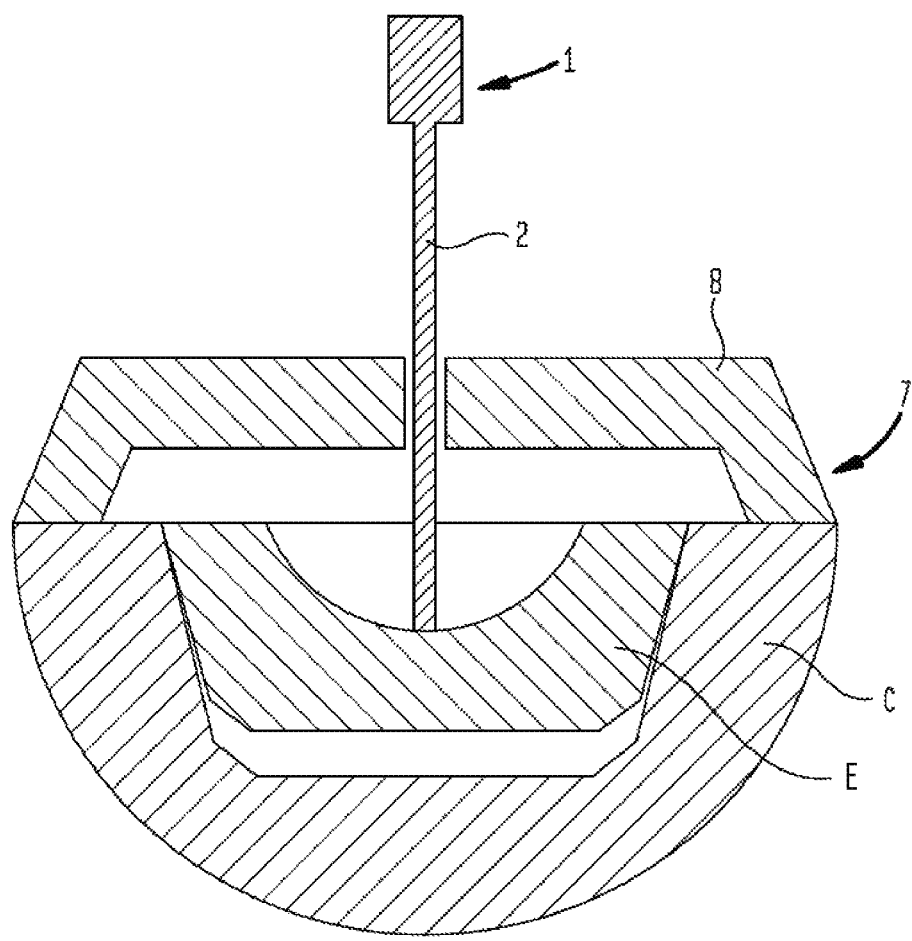
FIG. 5 is a schematic view of the device in use with fragment collection means.

Referring to FIG. 5, there is illustrated a device 1 with an associated fragment collection means 7. In this embodiment, the fragment collection means 7 is conveniently provided in the form of cover 8, the cover 8 having a cup-shape and comprising a wall formed from a pierceable, "self-sealing" material such as a rubber. Pierceable materials are commonly used in medicine as lids on liquid containers from which it is intended that liquids may be drawn by syringe without the need to open the lid. The material used to form the cover 8 is preferably transparent to assist in visualisation of the working area.

Figure 4:
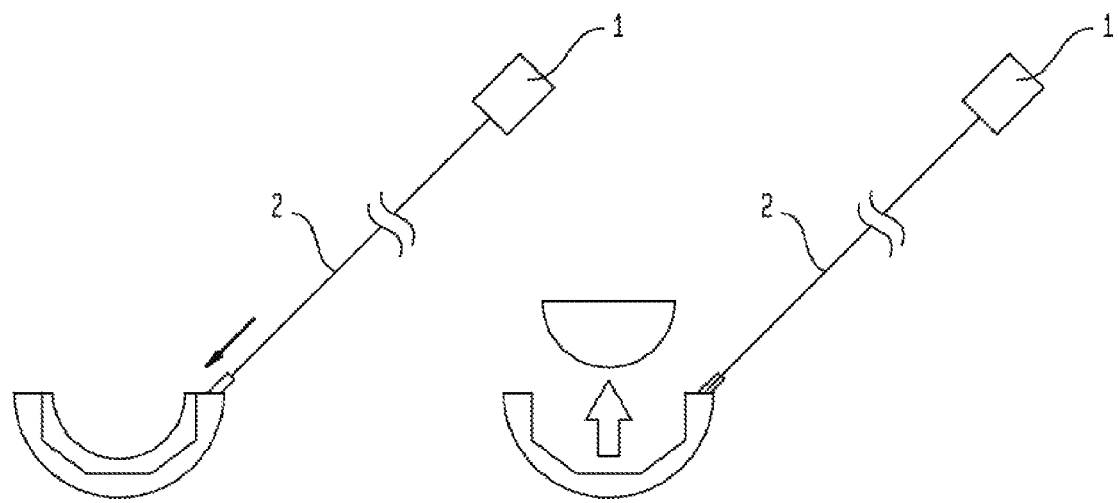
FIG. 4 is a schematic illustration of the device of FIG. 3 in use in a method in accordance with one aspect of the invention.

Referring to FIG. 4, in use, the probe 2 is inserted into the patient so that the tip of the probe contacts the metal part of the socket C, but not the insert E. The device 1 is actuated by releasing the lug which causes the spring to rapidly uncompress, forcing the striker element 5 against the proximal end of the probe, and thereby transmitting a shock wave along the probe to the metal part of the socket. Thus, a shock wave is administered of known and regulated amplitude. In many cases one or more further shock wave will be required, and the invention ensures that such further shock waves will also be of known and regulated magnitude. Due to the difference in the properties of the materials of the insert and the socket, the insert is easily released without danger of damage to the insert. However, should damage occur, or if the surgeon has no option but to break the insert for removal FIG. 5, cover 8 is provided to trap fragments of insert thereby prevent them from contaminating the area of the joint. The cover 8 is placed upside down, relative to the insert E so that it forms, with the metal part of the socket, a completely closed volume, trapping any fragments of insert within. As the wall of the cover 8 is transparent, the surgeon has a clear view of the working area, and as the wall is formed from a pierceable material, the probe 2 can be passed through it to contact the insert E without there being any requirement for an aperture in the wall through which insert fragments could escape. As a further expedient (not shown) the cover 8 can be formed or provided with a conduit through which fragments of insert can be removed by, for example application of a vacuum whilst the cover 8 is in situ.

Thus it can be seen that in one embodiment the invention provides what may be termed an Orthopaedic Power Controlled Ancillary (OPCA) for artificial junction separation which consists of a medical device with pre-adjusted energy transmission The device generates a shock wave which is transmitted to the appropriate part of the junction. The shock wave transmission will be different in the different materials which allows or facilitates the separation of the parts.

It is thought that the power transmitted deforms the two parts differently or one part and not the other part in order to create the separation.

It is further thought that the power transmitted may create a vibration in the materials which may also cause or facilitate the separation.

It is furthermore a possibility that the very fast displacement of one of the parts may cause or facilitate the separation.

The device according to the invention may be used with one hand only freeing up the surgeon's other hand.

It will be appreciated that the appropriately calibrated shock is adjusted to be safe for the bone, so that only the necessary quantity of energy is delivered. In addition the speed transmission is very high, with a small displacement allowing bone protection. Furthermore, a pre-adjusted level of energy can used by the system depending on the application.

Thus in a hip replacement or revision the device allows separation of the ceramic insert from the metal socket using a shock on the metal part, the device allows separation of the hip head artificial junction, the device can be used for insertion of orthopaedic nails and the device allows removal of metallic parts on or in bones.

Figure 6:
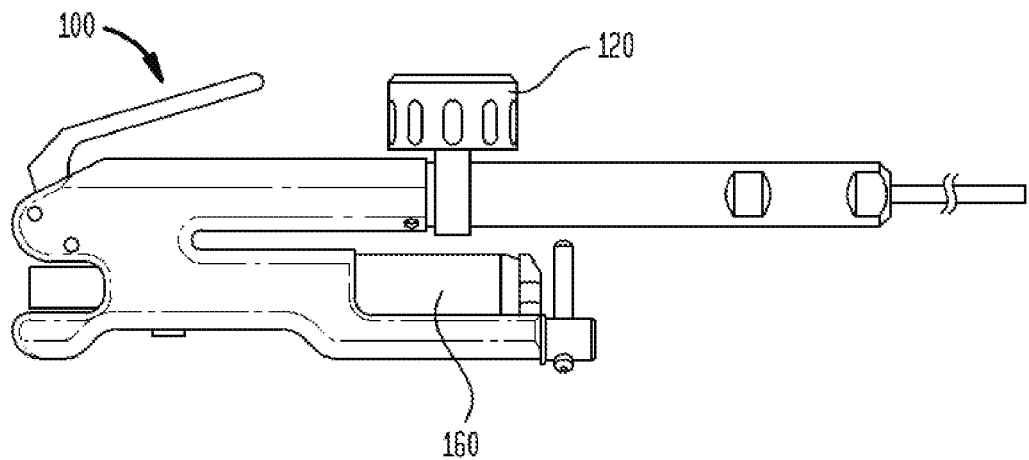
FIG. 6 is a side view of a pneumatic medical device according to the present invention.
Figure 7A:
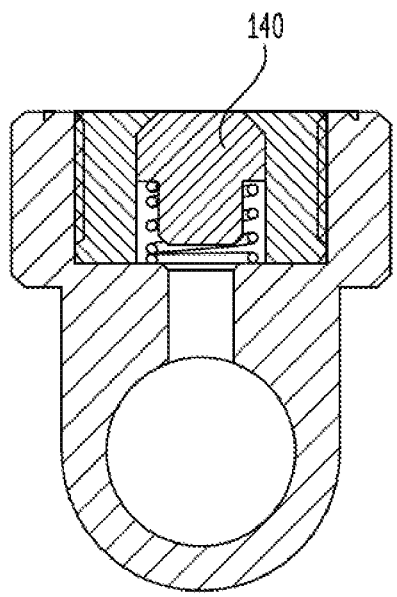
FIGS. 7a and 7b are cut away views of exhaust valves according to the present invention.
Figure 7B:
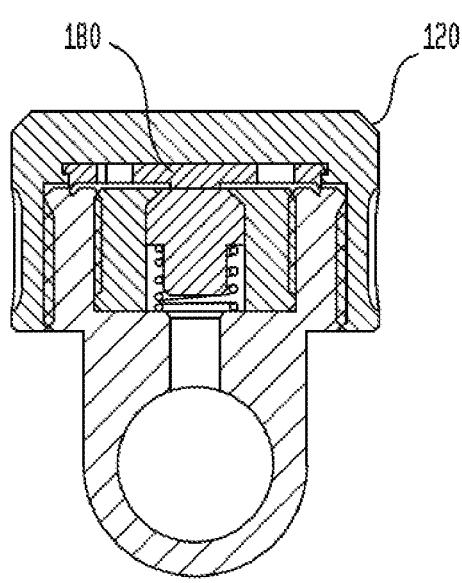

Referring to FIGS. 6, 7a and 7b, there is illustrated a pneumatic medical device 100, which device has a detachable exhaust filter assembly 120 attached to it such that the exhaust valve 140 is open allowing exhaust gases to be expelled from the device.

Prior to use a gas cartridge 160 is fitted to the device 100. In use, pressurised gas is admitted into the device 100 through an entry orifice (not shown) and used to drive a part of the device, e.g. a probe. Once used, the pressurised gas is expelled from the device 100 through the filter 180 of the detachable exhaust filter assembly 120. The filter 180 prevents contaminants, such as grease, from contaminating the sterile area in which the device 100 is being used. Once a medical practitioner has finished using the device 100, the gas cartridge 160 and the detachable exhaust filter assembly 120 are detached from the device 100 and may be discarded. The device 100 is then cleaned and sterilised so that it is ready for re-use.

The liquids used to clean and sterilise the outer surfaces of the device 100 do not contact the inner mechanisms of the device because they cannot enter the device 100. This is because the entry orifice is impermeable to liquids and the exhaust valve 140 is closed because a detachable exhaust filter assembly is not attached to the device 100.

The invention claimed is:

1. A pneumatic surgical device, comprising:
   means for generating an impulse force comprising a striker and an actuator;
   a removable probe comprising proximal and distal ends;
   a gas cartridge mounted on the surgical device and containing pressurized gas;
   detachable exhaust gas filter assembly; and an exhaust valve;

wherein the distal end of the probe is configured and shaped to engage at least a portion of an implanted medical part, the means for generating an impulse force is configured to deliver a mechanical impact force to the proximal end of the probe when the actuator is triggered by a user and pressurized gas is thereby released from the gas cartridge to cause the striker to deliver the impact force to the proximal end of the probe, the impact force delivered by the distal end of the probe falls within a reproducible preset range, pressurized gas originating from and released by the gas cartridge is expelled through an exhaust valve and thence through an exhaust gas filter included in the exhaust gas filter assembly, the exhaust gas filter is configured to prevent grease or other contaminants in the pressurized gas from passing into a sterile area external to the surgical device, the exhaust valve is configured to adopt an open position only when the detachable exhaust gas filter assembly is attached to the device and the exhaust valve is further configured to adopt a closed position when the detachable exhaust gas filter assembly is not attached to the device, the exhaust valve being biased in the closed position when the detachable exhaust pas filter assembly is not attached to the device.

2. The pneumatic surgical device of claim 1, the means for generating an impulse force being configured to generate the impact force upon each actuation thereof.

3. The pneumatic surgical device according to claim 1, wherein the exhaust gas filter assembly is sterilizable.

4. The pneumatic surgical device of claim 1, wherein the detachable exhaust gas filter assembly comprises a screw thread configured to mate with a complementary screw thread on the surgical device.

5. The pneumatic surgical device of claim 1, wherein the detachable exhaust gas filter assembly further comprises a resiliently deformable element, such that the detachable exhaust gas filter assembly is configured to be pushed onto the device to attach the detachable exhaust gas filter assembly to the device, and the resiliently deformable element is further configured to be squeezed and to deform when the detachable exhaust gas filter assembly is detached and pulled away from the surgical device.

6. The pneumatic surgical device of claim 1, wherein the detachable exhaust gas filter assembly comprises an internal ring configured to push against and cause the exhaust valve to open when the detachable exhaust gas filter assembly is attached to the surgical device.

7. The pneumatic surgical device of claim 1, wherein the exhaust valve is configured to withstand a temperature between 100° C. and 140° C. and a pressure between 2.5 bars and 3 bars.

8. The pneumatic surgical device of claim 1, further comprising an entry orifice for the gas, wherein the entry orifice is configured to permit the gas to be expelled when the device is not in use.

9. The pneumatic surgical device of claim 8, wherein the entry orifice comprises an entry valve or entry filter.

10. The pneumatic surgical device of claim 8, wherein the entry orifice further comprises a hydrophobic material or PTFE.

11. The pneumatic surgical device of claim 8, wherein the entry orifice is configured to withstand a temperature between 100° C. and 140° C. and a pressure between 2.5 bars and 3 bars.

12. The pneumatic surgical device of claim 1, wherein the exhaust gas filter comprises a biological filter.

13. The pneumatic surgical device of claim 1, wherein the detachable exhaust gas filter assembly is configured to be disposable.

14. The pneumatic surgical device of claim 1, wherein the detachable exhaust gas filter assembly is configured to be attached to the surgical device a single time to prevent reuse.

15. The pneumatic surgical device of claim 14, wherein the detachable exhaust gas filter assembly further comprises a part configured to shear upon detachment of the detachable exhaust filter assembly from the surgical device such that the detachable exhaust gas filter assembly can no longer be attached to the surgical device.

16. The pneumatic surgical device of claim 1, further comprising means for collecting fragments of the implanted medical part upon breakage thereof.

17. The pneumatic surgical device of claim 16, wherein the means for collecting fragments comprises a cover configured to surround at least portions of the implanted medical part.

18. The pneumatic surgical device of claim 16, wherein the means for collecting fragments comprises a pierceable shroud or veil configured to surround at least portions of the implanted medical part.

19. The pneumatic surgical device of claim 18, wherein the means for collecting fragments comprises a pierceable cup configured to surround at least portions of the implanted medical part.

20. A method for separating, adjusting or attaching two or more parts or materials in a surgical procedure, the method comprising applying an impulse force to at least one of said materials or parts using the device of claim 1.

21. The method according to claim 20, wherein the method further comprises a total hip replacement or a hip replacement revision procedure.

22. The method according to claim 20, wherein the method further comprises the use of means for collecting a fragment.

* * * * *